United States Patent [19]

Horvath

[11] 4,186,449
[45] Feb. 5, 1980

[54] SWIVEL JOINT

[75] Inventor: Eduard Horvath, Vienna, Austria

[73] Assignee: Otto Bock Orthopädische Industrie KG, Duderstadt, Fed. Rep. of Germany

[21] Appl. No.: 892,260

[22] Filed: Mar. 31, 1978

[30] Foreign Application Priority Data

Apr. 4, 1977 [AT] Austria .................................. 2337/77

[51] Int. Cl.² .......................... A61F 1/08; A61F 1/04
[52] U.S. Cl. .................................................. 3/2; 3/21;
3/30; 3/35; 403/111; 403/146; 403/165
[58] Field of Search ............................ 3/2, 21, 30–35;
403/111, 146, 165

[56] References Cited

U.S. PATENT DOCUMENTS

| 3,706,465 | 12/1972 | Olowinski | 3/2 X |
| 3,906,552 | 9/1975 | Weber | 3/2 X |
| 3,956,775 | 5/1976 | Moore | 3/2 X |
| 4,038,705 | 8/1977 | Owens et al. | 3/2 |

*Primary Examiner*—Ronald L. Frinks
*Attorney, Agent, or Firm*—Karl F. Ross

[57] ABSTRACT

A swivel joint for a leg prosthesis has its relatively rotatable members urged into a neutral position by a multiple-disk compound axial compression spring bearing upon balls which ride along inclined ramps upon relative rotation of the members.

9 Claims, 5 Drawing Figures

SWIVEL JOINT

FIELD OF THE INVENTION

This invention relates to a swivel joint, especially for artifical leg limbs, comprising two relatively rotatable members, which bear on each other with thrust bearings e.g., rolling element bearings, rotatable from a neutral position in opposite senses against the influence of an elastic restoring element.

BACKGROUND OF THE INVENTION

Such swivel joints are subjected to torsional stress and to a compressive stress in the direction of the pivotal axis of the joint and are often subjected to other stresses as well. These stresses give rise to problems in the design of such joints. Particularly when such joints are intended for artifical leg limbs, such stresses in addition to the usual torsional and compressive stresses may have a large magnitude, which often cannot be exactly ascertained numerically.

It is known from anatomy that a human being who is walking not only bends, stretches, abduces and adduces the legs but at the same time twists them about the mechanical longitudinal axis of the leg. In a normal, straight leg, this torsional axis or mechanical longitudinal axis extends from the center of the upper ankle joint through the center of the knee joint to the centre of the hip joint.

During walking, the legs are twisted most strongly in the hip joint and partly in the knee joint, but also in the joints of the foot. These movements, which can generally be described as twisting movements, are superimposed on opposite movements of the pelvis. The torsional axis is not normal to the surface which supports the leg but is inclined to that surface. As a result, the leg is not only twisted but a lateral inclination is imparted to the axis when the leg is stepping forward and when the foot is rolling on the ground. During the movement of the leg, the torsional axis thus describes a conical surface. The inclination is imparted to the axis about the upper ankle joint so that walking results in the known displacement of the center of gravity transversely to the direction of advance. The centre of gravity of the body of a person who is walking thus performs a sinusoidal movement with respect to the direction of advance.

After an amputation, the patient loses the ability to walk properly. He is then given training in which he learns to perform the described movement with the artificial limb, although this results in a rotation torsion between the soft envelope of the stump and the inside wall of the artificial limb in contact with said stump. This torsion gives rise to an irritation of the skin of the stump and to further inconveniences.

Various attempts have been made to design rotators which enable the patient to walk as naturally as possible and which avoid an irritation of the flesh of the stump (which may be a thigh stump or a tibia stump). Designs have been proposed in which the two relatively movable members bear on each other with interposed ball bearings while an elastomeric torsion spring exerts a restoring torque between the two members which are rotatable relative to each other. In such experimental swivel joints the elastomeric spring consists of an elastomeric ring, which is disposed between two end plates. The two end plates are secured to the two rotatable members fo the swivel joint. In another known design the axial gap between the relatively rotatable members is covered by a hoselike element, which is connected at its opposite ends to the relatively rotatable members by hose clamps. All these designs have the disadvantage that they are too heavy for practical use. Certain advantages for thigh-amputated patients have been afforded by such designs in experiments, particularly as regards the lessening of the irritation of the skin. However, the above-mentioned experimental designs do not appear to be suitable for tibia-amputated patients because they can bend the knee without difficulty when standing.

OBJECT OF THE INVENTION

It is an object of the invention to provide a swivel joint which is sufficiently strong and light weight and can be used universally not only under a strictly axial torsional stress and bending stress but also under stresses in addition to those mentioned above.

SUMMARY OF THE INVENTION

In a swivel joint of the kind mentioned first hereinbefore, this object is accomplished according to the invention in that the restoring element consists of a compression spring, which bears at one end on a sleeve axially slidable and non-rotatable in one of the relatively rotatable members and which bears on ramps of the adjacent (second) rotatable member, particularly with interposed balls, which engage one end face of the sleeve, so that the distance between the sleeve and the adjacent member of the swivel joint can be varied during a relative rotation of the two members of the hinge joint and the spring stress will vary with this distance.

With this design of the swivel joint, a distortion of the soft parts adjoining the artificial limb can be effectively avoided or at least considerably reduced. The swivel joint according to the invention ensures that the twisting movements of the leg will be performed in a horizontal plane. The specific design, by which the relative movement is redirected, causes twisting movements to be redirected into the vertical and to be applied to the compression spring and taken up resiliently. The compression spring consists preferably of a multiple-disc spring stack.

The joint has a predetermined orientation in position of rest so that after a rotation at the joint, the artifical limb will return to a neutral position, which is determined during the manufacture or fitting of the artificial limb.

The distribution of forces will be improved and the forces acting on the swivel joint will be equalized if, according to a further feature of the invention, the ramps extend from a surface of one of the two rotatable members which is normal to the pivotal axis of the joint, and the ramps have a zig-zag or undulatory configuration in a cylindrical section which is coaxial to the pivotal axis of the joint and developed into a plane. If desired, mating ramps are provided on the end face of the sleeve which faces that surface of said one rotatable member which is normal to the pivotal axis of the joint. The pressure which results from the deflection of the force (pressure force) which is applied is then taken up by a multiplicity of ramps so that the stresses are equalized and the total pressure is divided into several component pressures which are distributed around the torsional axis.

To permit of a variation of the spring characteristic throughout the spring excursion, the compression spring is provided with a radial projection, which is preferably annularly closed and extends into a gap between two axially spaced apart stops. With this design, the spring is effective only over part of its length during part of the movement and is effective over its entire length during another part of the movement, so that the compression spring is equivalent in action to two springs which have different spring constants and act at different times or during different parts of the movement.

A simple, space-saving arrangement will be obtained if one stop for the radial projection of the compression spring consists of a radial surface, particularly the end face of a cylinder, which is surrounded by the compression spring over part of the length of the spring and protrudes from that surface of said one rotatable member which is normal to the pivotal axis of the joint and provided with the ramps. The second stop can be adjustable relative to the first stop along the pivotal axis of the joint and is adapted to be fixed in position so that the freedom of axial movement of the projection connected to the compression spring can be varied and the spring constant can thus be varied too. A symmetrical spring characteristic for a rotation to the left and right can be obtained if the inclination (rise) relative to the horizontal of the ramps which rise to the right differs from the inclination (rise) relative to the horizontal of the ramps which rise to the left.

To provide for a compact structure, the adjustable stop consists of a radial shoulder, which is provided on a bushing, which is slidably mounted in the cylinder provided with the other stop, and said bushing is preferably non-rotatably connected (keyed) to the cylinder. The bushing may be displaced in the direction of the hinged axis by means of a screw, which is rotatably mounted in the rotatable member provided with the ramps. The screw is preferably accessible from the pivotal axis of the joint so that the spring can easily be adjusted.

In order to prevent a lateral tilting of the forward portion of the foot during a walking movement, a further feature of the invention resides in that the rotation of the relatively rotatable members relative to each other is limited, preferably within an angular range of ±20° about the neutral position. To that end, both rotatable members may have radial projections which extend into a common plane that is normal to the pivotal axis of the joint, and in the neutral position of the relatively rotatable members the radial projections of one rotatable member are offset from the radial projections of the other rotatable member by an angle which is equal to the permissible angular movement.

Swivel joints for artificial limbs should be light in weight and for this reason, should be as small as possible. This requirement means that the swivel joint should be able, in spite of its small size, to take up the loads to be applied to it. The thrust bearings are particularly susceptible to heavy loads. In order to prevent an overloading of and damage to the thrust bearings, a further feature of the invention resides in that one rotatable member has a projecting flange, which extends between two annular series of rolling elements, which are guided on raceways formed on the other rotatable member, and the rotatable member which is provided with the projecting flange is provided with preferably annular backing surfaces, which are associated with respective ones of the annular series of rolling elements and, when the swivel joint is relieved, the backing surfaces are clear of engaging surfaces, which are provided on the adjacent rotatable member and adapted to cooperate with the backing surfaces, whereas under an overload the clearance is eliminated as a result of the elastic deformation of the rolling elements and/or of the portions provided with the raceways for the rolling elements so that the backing surface or surfaces then engage the engaging surfaces axially confronting them.

BRIEF DESCRIPTION OF THE DRAWING

The invention will now be described more fully with reference to an embodiment shown by way of example in the annexed drawing, in which.

SPECIFIC DESCRIPTION

Figure 1:
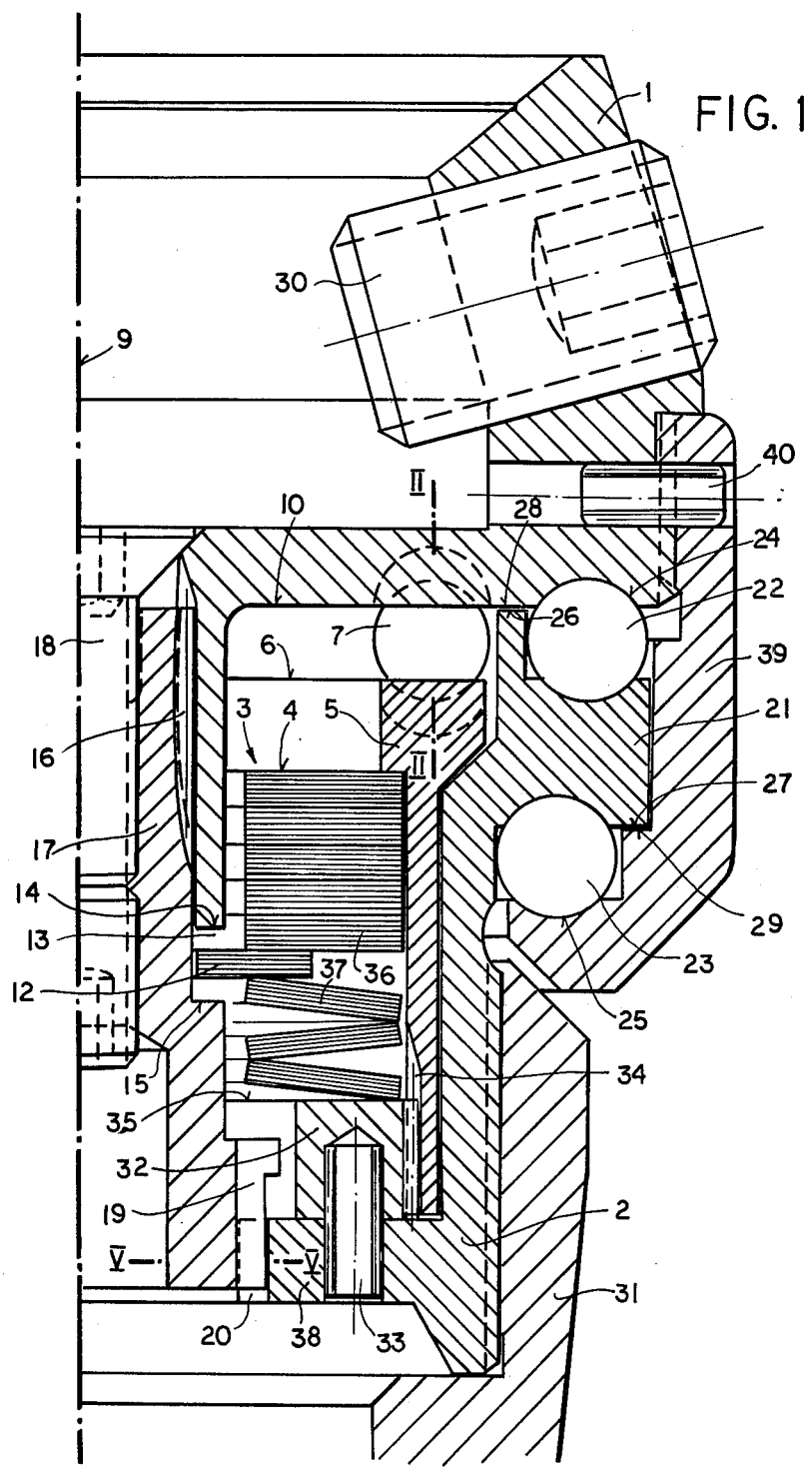
FIG. 1 is an axial cross-sectional view through one half of a swivel joint according to the invention.
Figure 3:
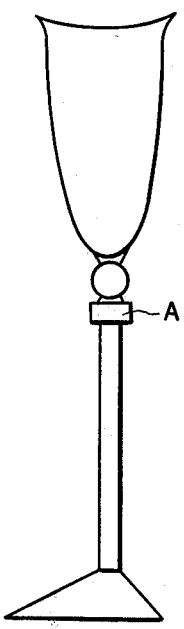
FIG. 3 shows diagrammatically the use of a swivel joint according to the invention with an artificial limb for a thigh-amputated patient.
Figure 5:
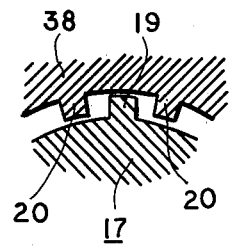
FIG. 5 is a fragmentary sectional view taken on line V—V of FIG. 1.
Figure 4:
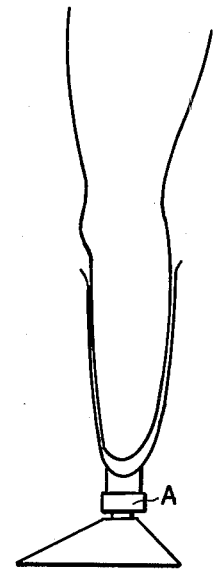
FIG. 4 shows the use of a swivel joint according to the invention with an artificial limb for a tibia-amputated patient.

In the drawing, two relatively rotatable members of the swivel joint according to the invention are designated 1 and 2. By means of screws 30, a fitting for connection to the shaft of the artificial limb is held in position on member 1. The fitting can be centered by means of the screws 30. An artificial foot can be screw-threadedly connected to the member 2, e.g., by means of a nut 31.

Where an artificial thigh is employed (FIG. 3), the member 2 may thus be connected to a tube, which carries the foot at its end (see FIGS. 3 and 4, in which the hinge joint is designated (A).

The two relatively rotatable members 1 and 2 are adapted to be deflected in opposite directions from a neutral position against the action of an elastic restoring element, which consists of a compression spring generally represented at 3. In the embodiment shown by way of example, the compression spring consists of a multiple or compound compression spring. The compression spring 3 bears at one end 4 on a sleeve 5, which is axially slidably and non-rotatably mounted on (keyed to) the member 2 of the swivel joint.

The sleeve 5 is axially slidably and non-rotatably mounted in that a ring 32 which is coaxial to the pivotal axis 9 of the swivel joint is connected by pins 33 to the rotatable member 2. The ring 32 is provided at its peripheral surface with serrations or with axial grooves (spline grooves), which receive tongues or splines 34, which are provided on the inside of the sleeve 5.

The second end of the compression spring 3 bears on the end face 35 of the ring 32. By means of balls 7 or other rolling elements engaging the inner end face 6 of the sleeve 5, the latter bears on ramps 8 of the adjacent rotatable member 1.

During a pivotal movement of the rotatable member 2 relative to the rotatable member 1, the balls 7 run up on the ramps 8 so that an axial movement is imparted to the sleeve 5 and the axial distance between the sleeve 5 and the rotatable member 1 is changed and with it the stress of the spring 3 as well as the resistance to a rotation of members 1 and 2 relative to each other. The ramps 8 extend from a surface 10, which is provided on the rotatable member 1 and normal to the pivotal axis 9 of the joint, and in a cylindrical section which is coaxial to the pivotal axis 9 have a zig-zag or undulatory configuration when said section is developed into a plane. This is particularly shown in FIG. 2.

Figure 2:
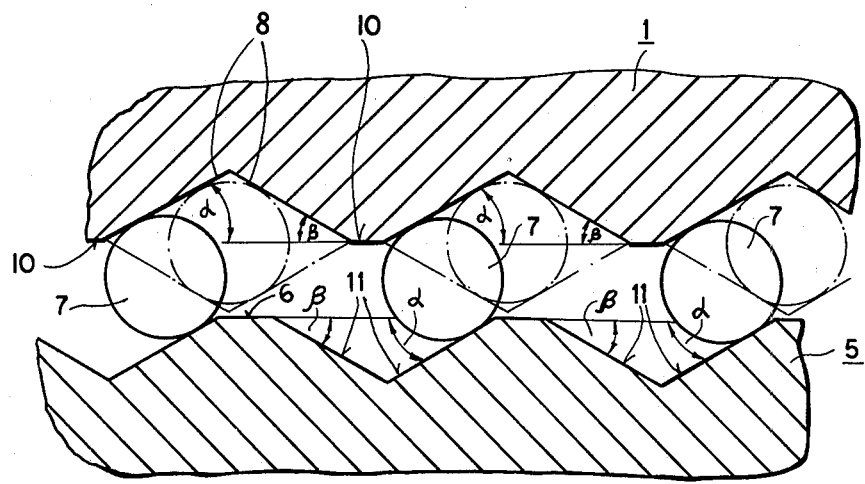
FIG. 2 is a sectional view taken on a cylindrical surface, which is indicated by line II—II of FIG. 1 and has been developed into a plane.

As is also apparent from FIG. 2, mating ramps 11 are provided on the sleeve 5 at its end face 6, which faces that surface 10 of the rotatable member 1 which is normal to the pivotal axis 9 of the joint. The compression spring 3 is provided with an annularly closed radial projection 12, which consists in the present case of one section of the multiple-disc spring and is smaller than the other sections of the multiple-disc spring 3 and extends between two adjacent sections 36, 37 of said spring.

The projection 12 also extends into a gap 13 between two axially spaced apart stops 14 and 15. The stop 14 for engaging the projection 12 of the compression spring 3 consists of a radial end face of a cylinder 16, which protrudes from that surface 10 of the rotatable member 1 which is normal to the pivotal axis 9. The cylinder 16 is surrounded by the compression spring 3 over part of the length of the latter. The second stop 15 for engaging the projection 12 of the compression spring 3 is adjustable along the pivotal axis 9 of the joint and adapted to be fixed in position so that the axial distance between the stops 14 and 15 can be changed and an unsymmetrical spring characteristic can be provided for the two directions of rotation of the joint. The adjustable stop 15 consists of a radial shoulder on a bushing 17, which is slidable in the cylinder 16 and non-rotatably connected by a tongue-and-groove (spline) joint to the cylinder 16 and thus to the rotatable member 1. The bushing 17 can be exactly adjusted axially by means of a screw 18, which is rotatably mounted in the rotatable member 1.

To limit the pivotal movement of the rotatable members 1, 2 relative to each other, both rotatable members 1, 2 are provided with radial projections 19, 20, which extend in a common plane that is normal to the pivotal axis 9 of the joint. When the rotatable members 1, 2 are in their neutral position, the angular spacing of the radial projections 19, 20 corresponds to the permissible angular movement of the two rotatable members 1, 2 relative to each other.

The stop 19 consists of a rib on the outside peripheral surface of the bushing 17 and the cooperating stop 20 protrudes from an inwardly directed flange 38 of the rotatable member 2. The axial extent of the stops 19 and 20 must be such that they overlap also when the bushing 17 has been axially displaced.

The thrust bearing of the swivel joint consists of two axially spaced apart annular series of rolling elements 22 and 23. The rotatable member 2 has a projecting flange 21, which extends between the rolling elements 22, 23 of the annular series. The rolling elements are guided by raceways 24, 25 formed in the rotatable member 1. The raceway 25 is formed in a bell-shaped component 39, which is connected by pins 40 to that portion of the rotatable member 1 which is provided with that surface 10 which is normal to the axis 9 of the swivel joint. The projecting flange 21 is provided with annular backing surfaces 26, 27, which are associated with the annular series of rolling elements 22, 23, respectively. When the swivel joint is relieved, there are clearances between the backing surfaces 26 and 27 and the engaging surfaces 28 and 29, respectively, which are provided on the rotatable member 1 and adapted to cooperate with the backing surfaces. Under an overload, those clearances are eliminated owing to the elastic deformation mainly of the rolling elements 22 and 23 under the overload and/or the elastic deformation of the raceways 24 and 25. As a result, the overload is taken up mainly by the cooperation between the backing surface 26 and the engaging surface 28, and between the backing surface 27 and the engaging surface 29, and does not overstress the annular series of rolling elements.

If the inclinations ($\alpha$, $\beta$) of the ramps 11 and 8 which rise to the right differ from those of the ramps 11 and 8 which rise to the left, different forces will be exerted during rotations to the right and left, respectively.

I claim:

1. A swivel joint, especially for artificial leg limbs, said joint comprises:
   two relatively rotatable members having a pivotal axis;
   thrust bearings interposed between said members and enabling relative rotation of said members from a neutral position in opposite senses; and
   an elastic restoring element connected to said members and resisting relative rotation of said members, said element comprising a compression spring bearing at one end on a sleeve axially slidable and non-rotatable in a first of the relatively rotatable members and bearing on ramps of the second rotatable member via balls which engage one end face of the sleeve so that the distance between the sleeve and the adjacent member of the swivel joint can be varied during a relative rotation of the two members of the swivel joint and the spring stress will vary with said distance.

2. The swivel joint defined in claim 1 wherein the ramps extend from a surface of said second member normal to the pivotal axis, said ramps having an undulatory configuration in a cylindrical section which is coaxial to the pivotal axis when developed into a plane.

3. The swivel joint defined in claim 2 wherein mating ramps are provided on said end face of the sleeve, and the inclination relative to the horizontal of the ramps which rise in one direction differs from the inclination relative to the horizontal of the ramps which rise in the other direction.

4. The swivel joint defined in claim 2 wherein the compression spring is provided with a radial projection which is preferably annularly closed and which extends into a gap formed between two axially spaced apart stops.

5. The swivel joint defined in claim 4 wherein one of said stops consists of a radial surface formed by the end face of a cylinder which is surrounded by the compression spring over part of the height of the spring and protrudes from said surface, the other stop being adjustable relative to said one of said stops along the pivotal axis and being adapted to be fixed in position.

6. The swivel joint defined in claim 5 wherein said other stop is formed by a radial shoulder on a bushing slidably mounted in said cylinder and is nonrotatably connected to said cylinder, said other stop being displaceable along the pivotal axis by a screw rotatably mounted in the second rotatable member.

7. The swivel joint defined in claim 1 wherein the relative angular movement of said members is limited to an angular range of ±20° from said neutral position.

8. The swivel joint defined in claim 7 wherein both rotatable members have radial projections which lie in a common plane normal to the pivotal axis, in the neutral position of the radial projections of one member being offset from the radial projections of the other member by an angle which is equal to the permissible angular movement.

9. The swivel joint defined in claim 1 wherein said first rotatable member has a projecting flange which extends between two annular series of rolling elements which are guided on raceways formed on the second member, and the first rotatable member is provided with annular backing surfaces which are associated with respective ones of the annular series of rolling elements, and when the swivel joint is relieved are clear of engaging surfaces which are provided on the second member and are adapted to cooperate with the backing surfaces, under an overload the clearance being eliminated as a result of the elastic deformation of the rolling elements and/or of the portions provided with the raceways for the rolling elements so that the backing surface or surfaces then engage the engaging surfaces axially confronting them.

* * * * *